(12) United States Patent
Ray et al.

(10) Patent No.: US 9,163,009 B2
(45) Date of Patent: Oct. 20, 2015

(54) SALTS OF RALTEGRAVIR

(75) Inventors: Purna Chandra Ray, Pune (IN); Ashok Sopanrao Yadav, Pune (IN); Dnyaneshwar Tukaram Singare, Pune (IN); Surinder Kumar Arora, Pune (IN); Girij Pal Singh, Pune (IN)

(73) Assignee: Lupin Limited, Mumbai (IN)

( * ) Notice: Subject to any disclaimer, the term of this patent is extended or adjusted under 35 U.S.C. 154(b) by 0 days.

(21) Appl. No.: 14/009,178

(22) PCT Filed: Apr. 4, 2012

(86) PCT No.: PCT/IB2012/051651
§ 371 (c)(1),
(2), (4) Date: Oct. 1, 2013

(87) PCT Pub. No.: WO2012/137142
PCT Pub. Date: Oct. 11, 2012

(65) Prior Publication Data
US 2014/0155607 A1 Jun. 5, 2014

(30) Foreign Application Priority Data

Apr. 6, 2011 (IN) .............................. 511/KOL/2011

(51) Int. Cl.
*C07D 413/12* (2006.01)
*A61K 31/513* (2006.01)

(52) U.S. Cl.
CPC ............ *C07D 413/12* (2013.01); *A61K 31/513* (2013.01)

(58) Field of Classification Search
CPC .......................... C07D 413/12; A61K 31/513
USPC .......................................... 514/269; 544/319
See application file for complete search history.

(56) References Cited

U.S. PATENT DOCUMENTS 7,169,780 B2 * 1/2007 Crescenzi et al. ......... 514/235.8
7,754,731 B2 7/2010 Belyk et al.

FOREIGN PATENT DOCUMENTS

| WO | 2006060712 | A2 | 6/2006 |
| WO | 2010140156 | A2 | 12/2010 |
| WO | 2011024192 | A2 | 3/2011 |
| WO | 2011123754 | A1 | 10/2011 |
| WO | WO 2011/123754 | * | 10/2011 ........... C07D 413/12 |

OTHER PUBLICATIONS

Berge, et al., Pharmaceutical Salts, J. of Pharm. Sciences (1977).*

* cited by examiner

*Primary Examiner* — Erich A Leeser
(74) *Attorney, Agent, or Firm* — The Webb Law Firm

(57) ABSTRACT

The present invention provides novel salts of raltegravir, viz., meglumine salt, erbumine salt, ammonium salt, tris salt and L-arginine salt of raltegravir and processes for their preparation.

7 Claims, 10 Drawing Sheets

SALTS OF RALTEGRAVIR

CROSS-REFERENCE TO RELATED APPLICATIONS

Figure 1:
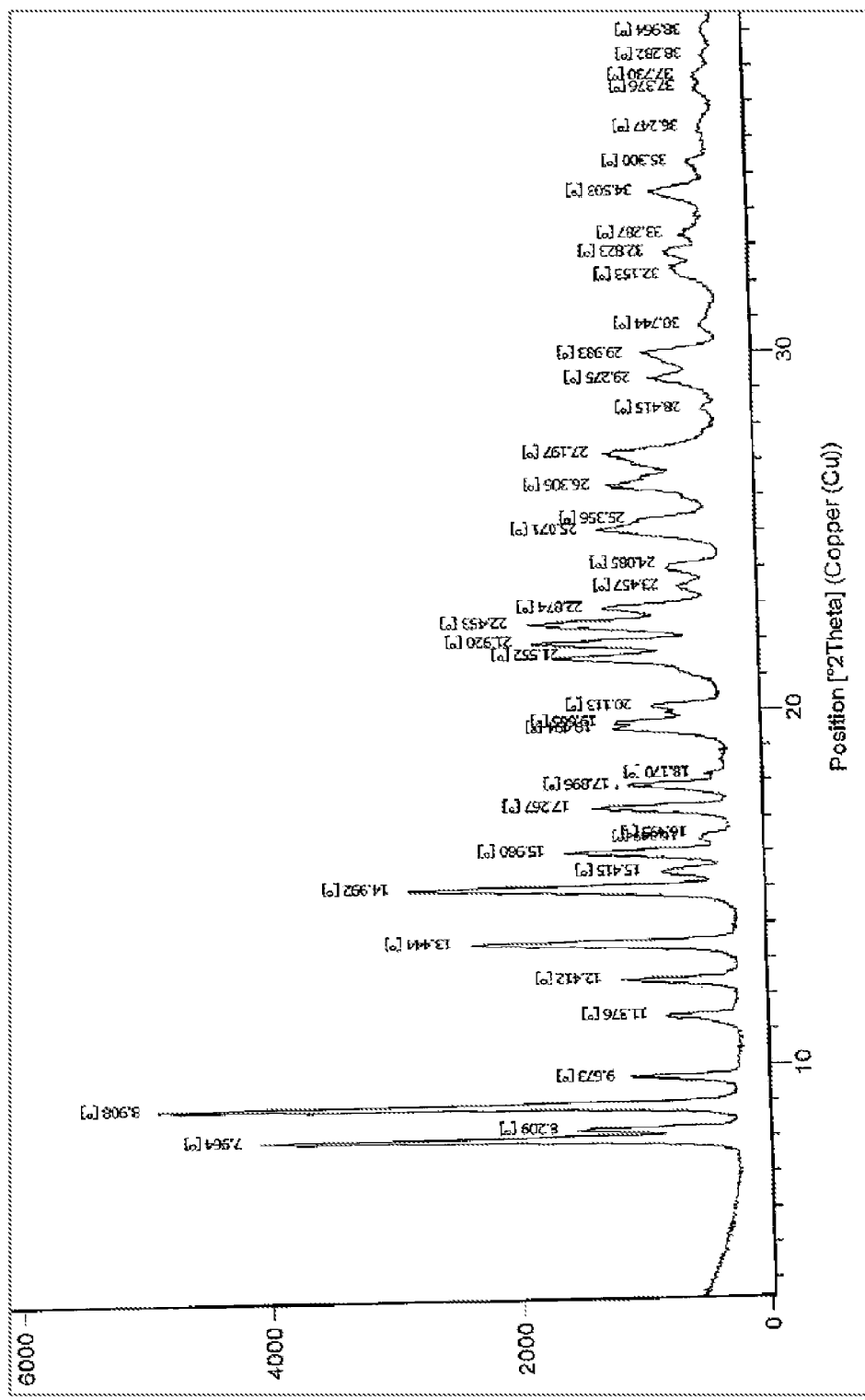

This application is the United States national phase of International Application No. PCT/IB2012/051651 filed Apr. 4, 2012, and claims priority to Indian Patent Application No. 511/KOL/2011 filed Apr. 6, 2011, the disclosures of which are hereby incorporated in their entirety by reference.

TECHNICAL FIELD OF INVENTION

The present invention provides novel salts of raltegravir and process for their preparation.

BACKGROUND OF THE INVENTION

Raltegravir is chemically known as N-(4-fluorobenzyl)-5-hydroxy-1-methyl-2-(1-methyl-1-{[(5-methyl-1,3,4-oxadiazol-2-yl)carbonyl]amino}ethyl)-6-oxo-1,6-dihydropyrimidine-4-carboxamide. Raltegravir is a potent HIV integrase inhibitor which is used for treatment of HIV infections, AIDS, and Aids Related Complex (ARC). The potassium salt of raltegravir, represented by the structural formula provided below, is marketed in USA under the trade name Isentress® by Merck & Co.

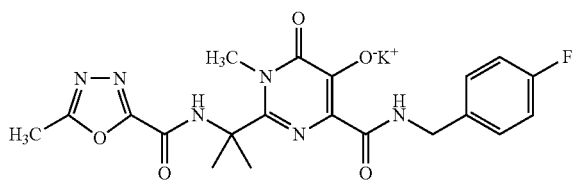

Raltegravir is generically and specifically disclosed in U.S. Pat. No. 7,169,780 B2 and potassium salt of raltegravir is specifically described by U.S. Pat. No. 7,754,731 B2. Raltegravir exhibits poor aqueous solubility where as the potassium salt of raltegravir is significantly more soluble in water and exhibit improved pharmacokinetics in animal models over raltegravir. On the contrary attempts to prepare crystalline sodium salt of raltegravir failed and resulted in an amorphous material.

Extensive study is carried out in pharmaceutical industry for development of different new salts and polymorphs of various drug substances, to obtain suitable salts and forms that possess improved performance characteristics such as aqueous solubility, improved bioavailability, chemical stability, shelf life etc.

Literature survey reveals that raltegravir potassium can exist in different polymorphic forms, which differ from each other in terms of stability, physical properties and pharmacokinetics. Very few documents in prior art are directed towards salts and polymorphs of raltegravir, which are incorporated here by way of reference.

The PCT application WO 2006/060712 A2 discloses two anhydrous crystalline forms of raltegravir potassium viz., form 1 and form 3 and one crystalline hydrate designated as form 2. Form 1 is especially known to exhibit superior bioavailability and improved pharmacokinetics over raltegravir. It can be prepared by crystallization of raltegravir potassium from a mixture of potassium base, raltegravir, water and an alcohol.

Hydrated crystalline form 2 is prepared by sonicating a mixture of raltegravir, KOH, acetone and trace amount of water whereas anhydrous crystalline form 3 is obtained by crystallization of amorphous raltegravir potassium from ethanol.

The PCT application WO 2010/140156 A2 describes amorphous form and crystalline form H1 of raltegravir potassium. The process for preparation of crystalline form H1 comprises of providing a solution of raltegravir potassium in dimethyl formamide, dimethyl acetamide or mixtures thereof and further separating and isolating the solid obtained. The amorphous form is obtained by freeze drying the aqueous solution of raltegravir potassium at −180° C.

WO 2011/024192 A2 describes novel crystalline form A, form B and amorphous form of raltegravir and processes for preparing them.

Salts often improve physical and biological characteristics of mother compounds without modifying primary pharmacological activity, based on mechanism of action. Thus there is a continuing need to obtain new salts of raltegravir having improved physical and/or chemical properties. The present invention satisfies this need by providing new salts of raltegravir with enhanced solubility in water or aqueous media as an essential property of active pharmaceutical ingredients determining the performance of pharmaceutical formulation.

DESCRIPTION OF ACCOMPANYING DRAWINGS

FIG. 1: illustrates X-ray powder diffraction pattern of crystalline meglumine salt of raltegravir.

Figure 2:
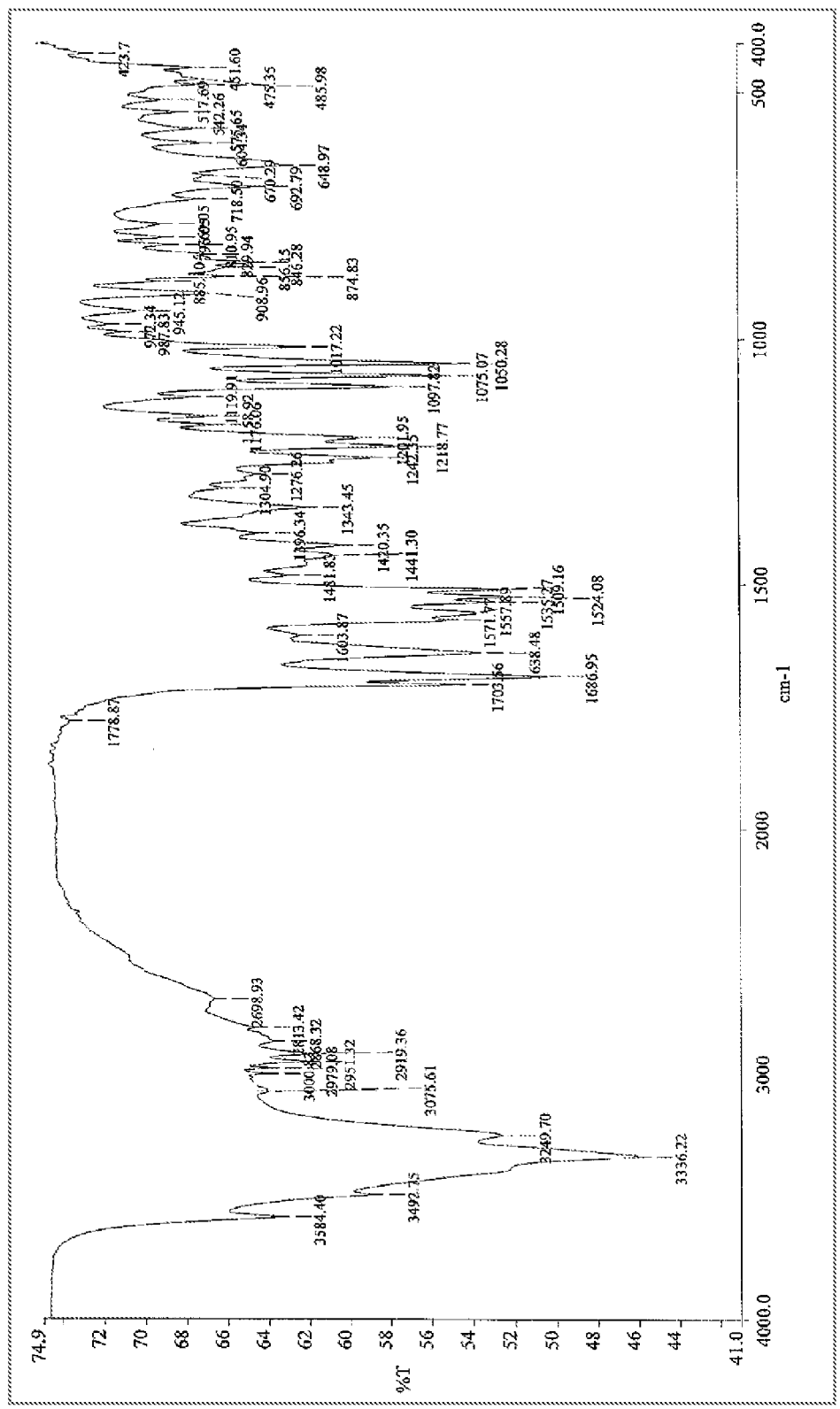

FIG. 2: illustrates IR spectrum for crystalline meglumine salt of raltegravir.

Figure 3:
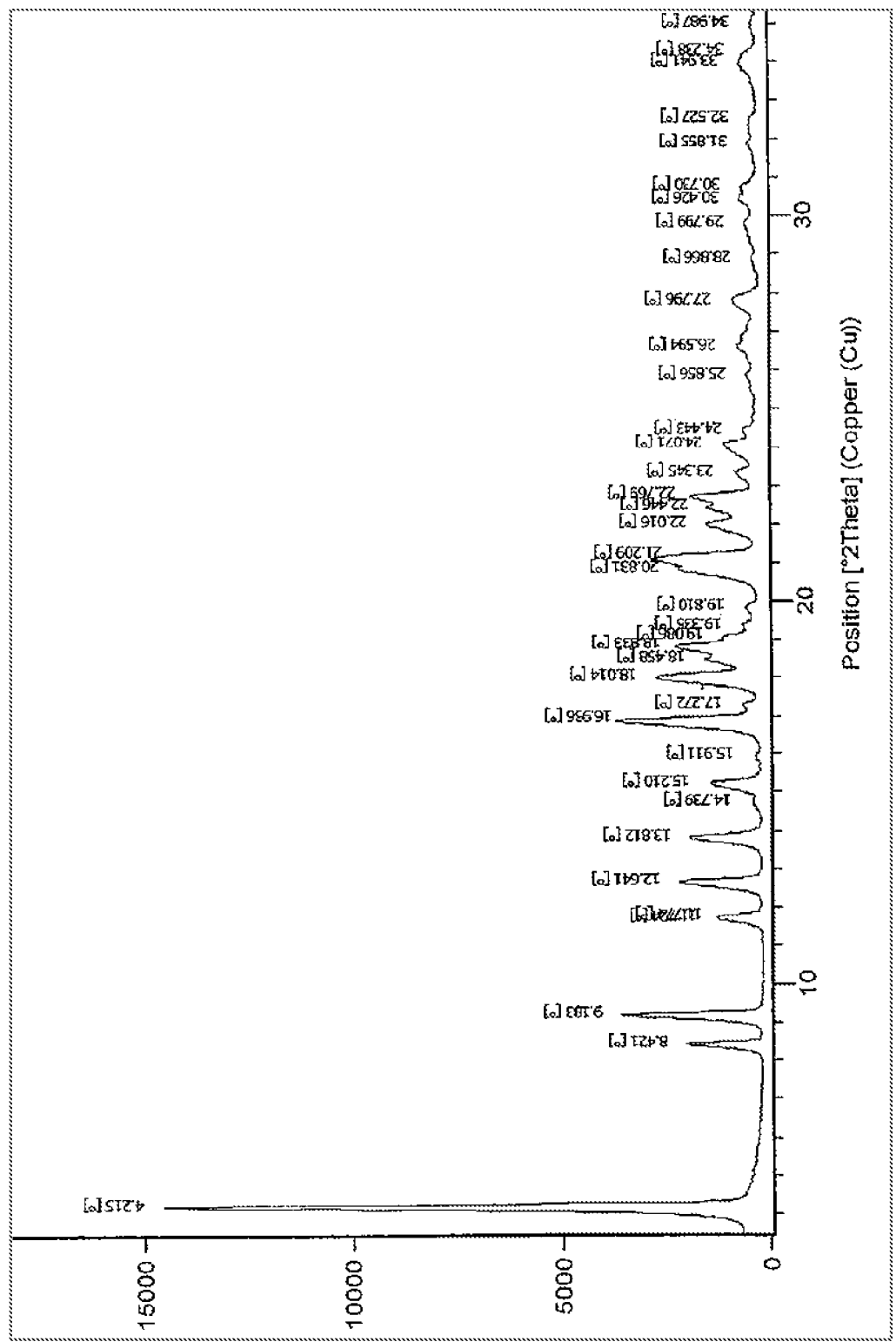

FIG. 3: illustrates X-ray powder diffraction pattern of crystalline erbumine salt of raltegravir.

Figure 4:
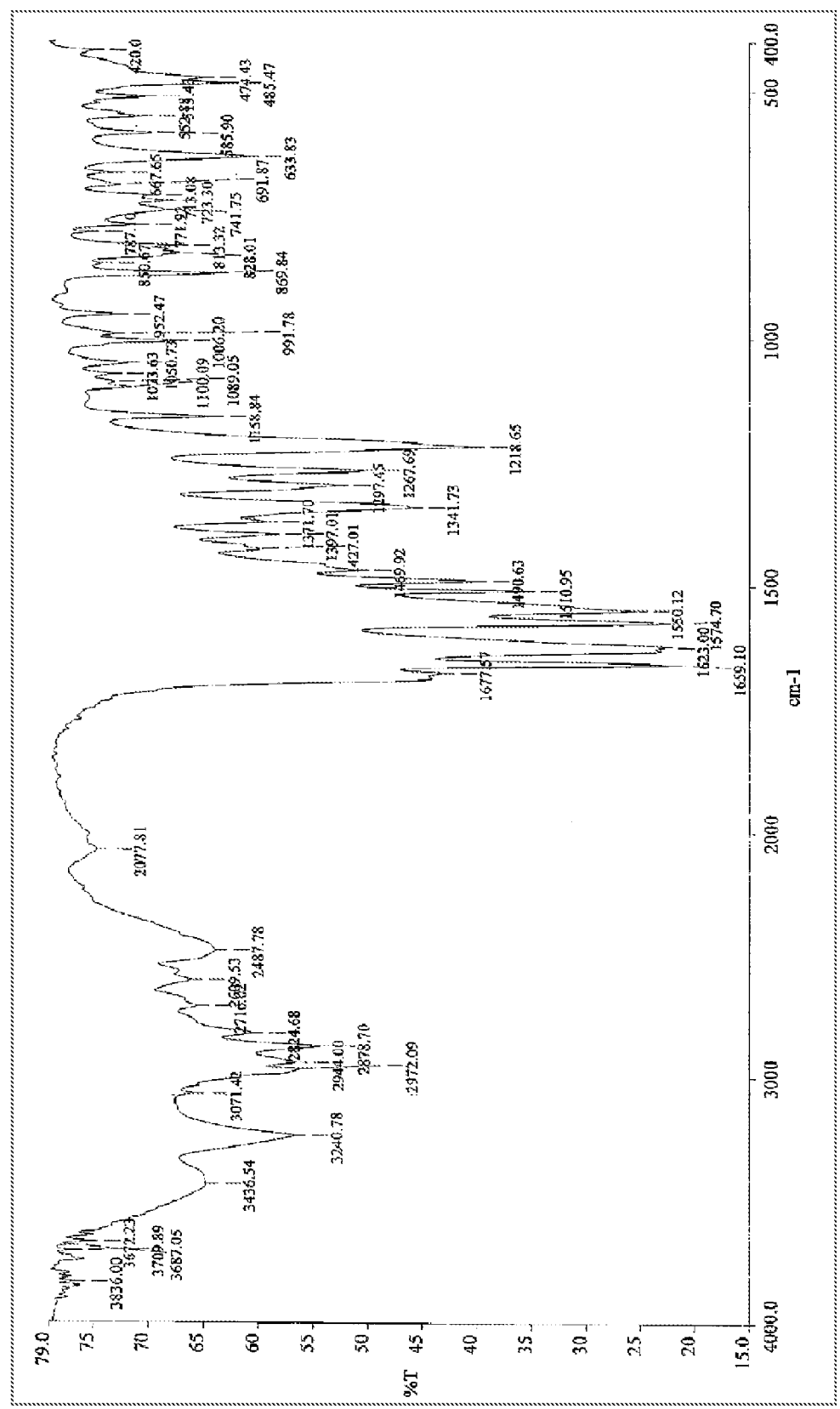

FIG. 4: illustrates IR spectrum for crystalline erbumine salt of raltegravir.

Figure 5:
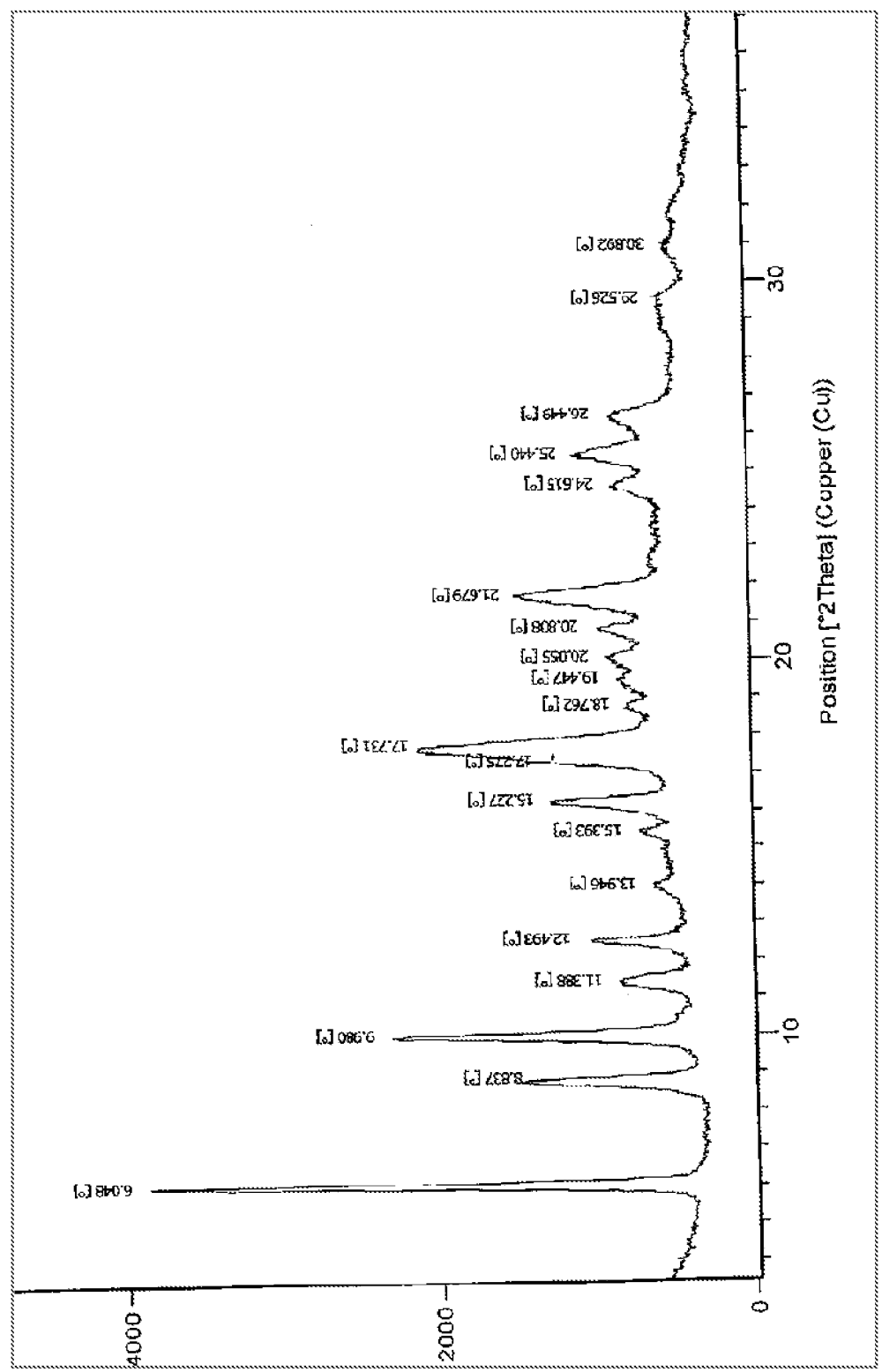

FIG. 5: illustrates X-ray powder diffraction pattern of crystalline ammonium salt of raltegravir.

Figure 6:
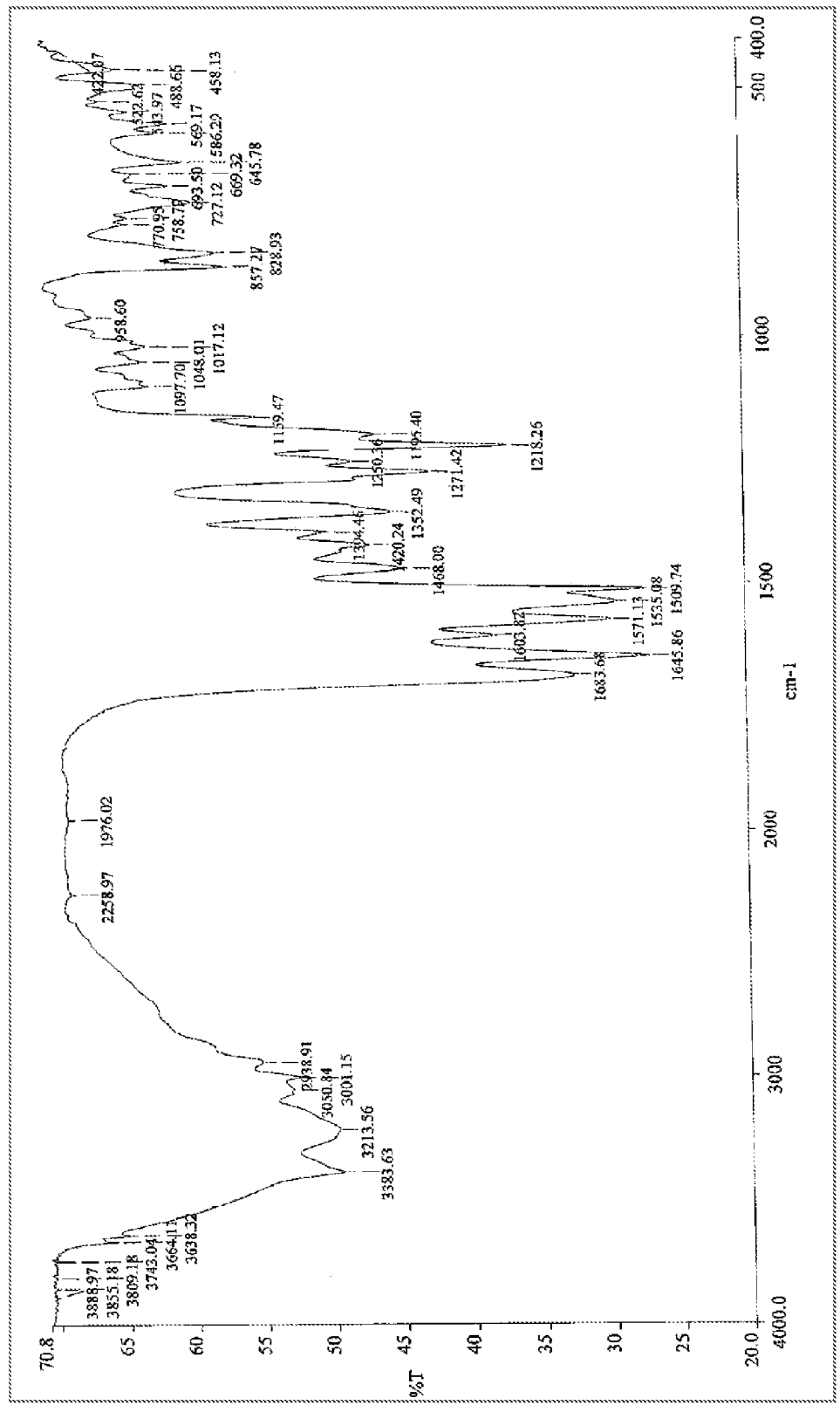

FIG. 6: illustrates IR spectrum for crystalline ammonium salt of raltegravir.

Figure 7:
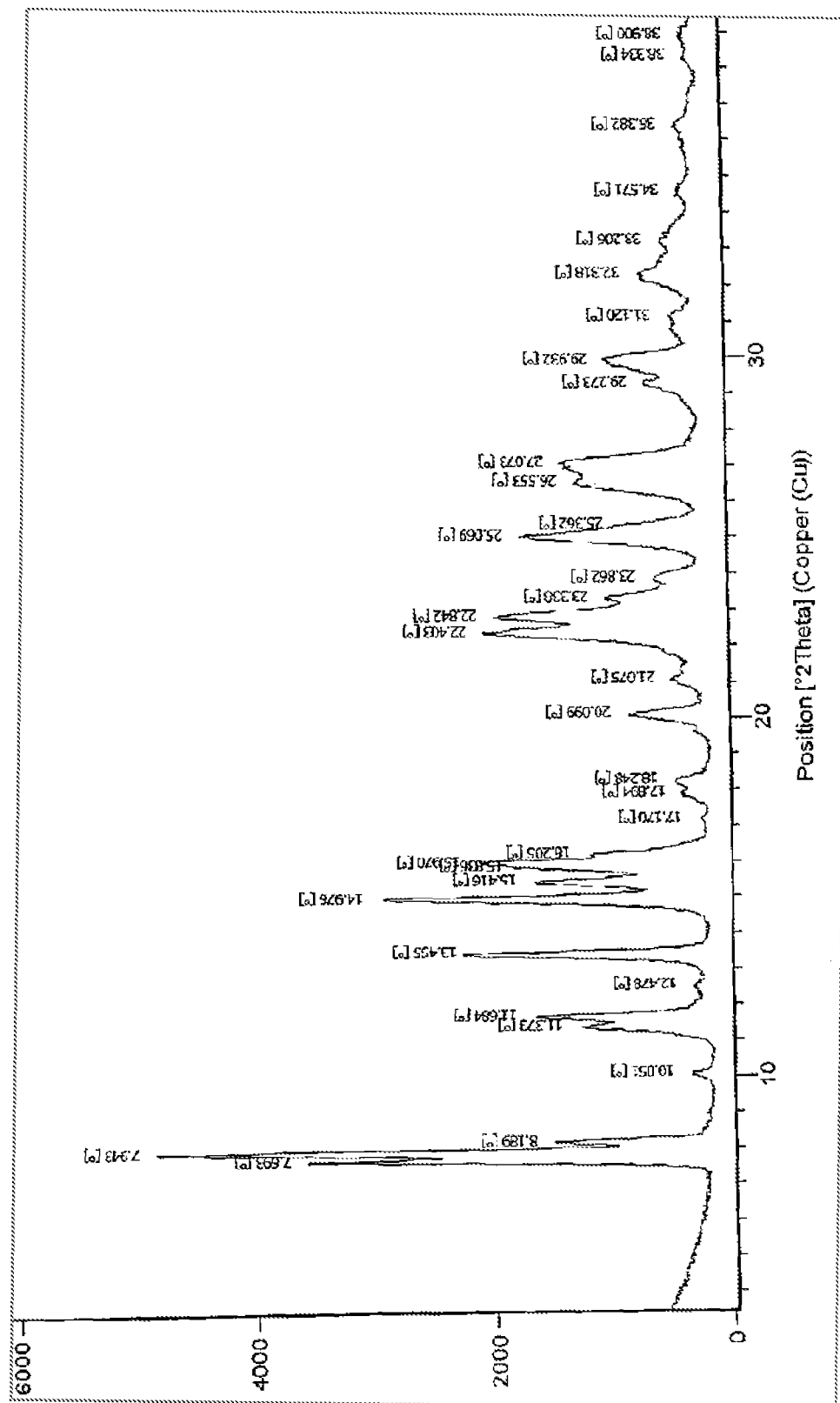

FIG. 7: illustrates X-ray powder diffraction pattern of crystalline tris salt of raltegravir.

Figure 8:
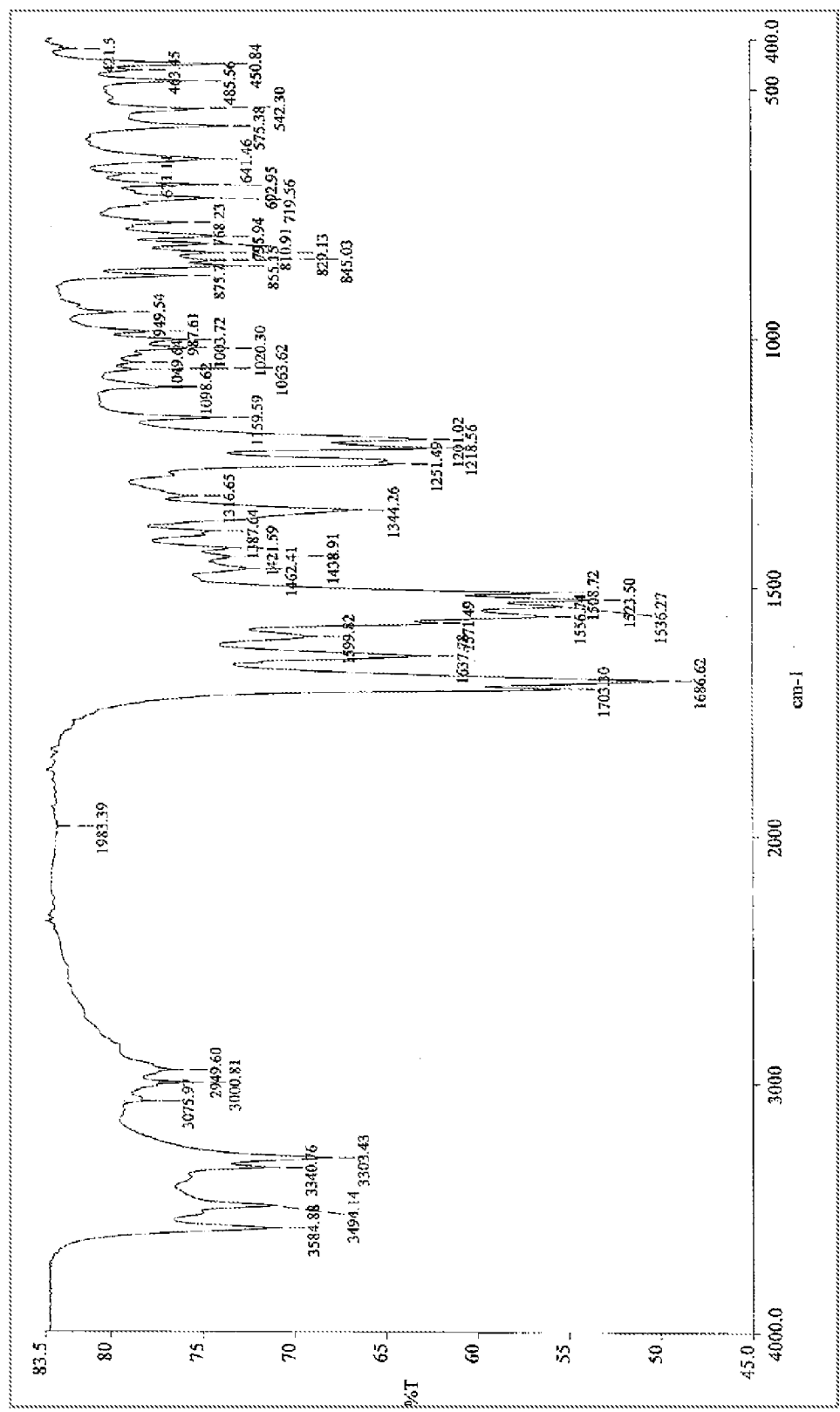

FIG. 8: illustrates IR spectrum for crystalline tris salt of raltegravir.

Figure 9:
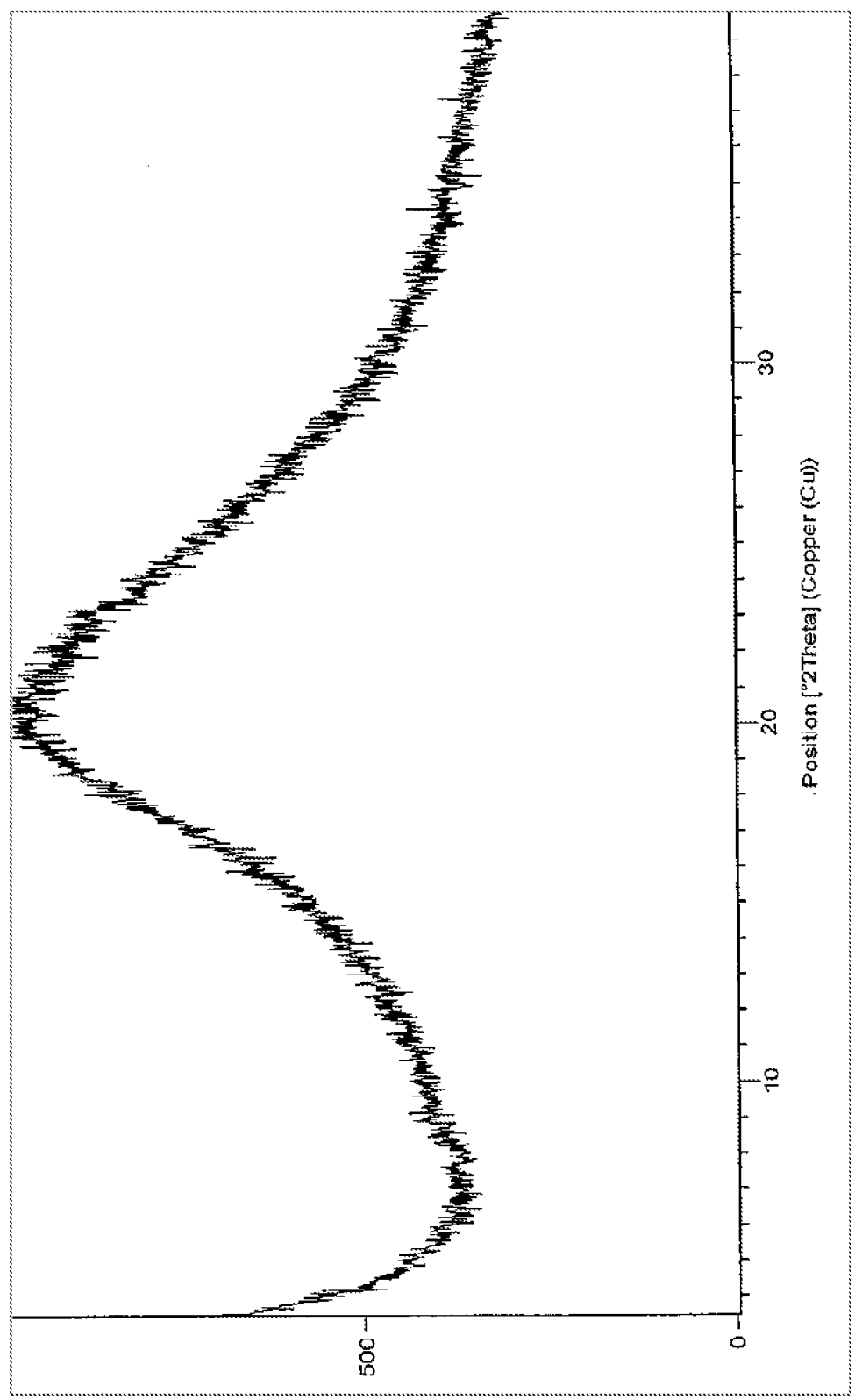

FIG. 9: illustrates X-ray powder diffraction pattern of amorphous L-arginine salt of raltegravir.

Figure 10:
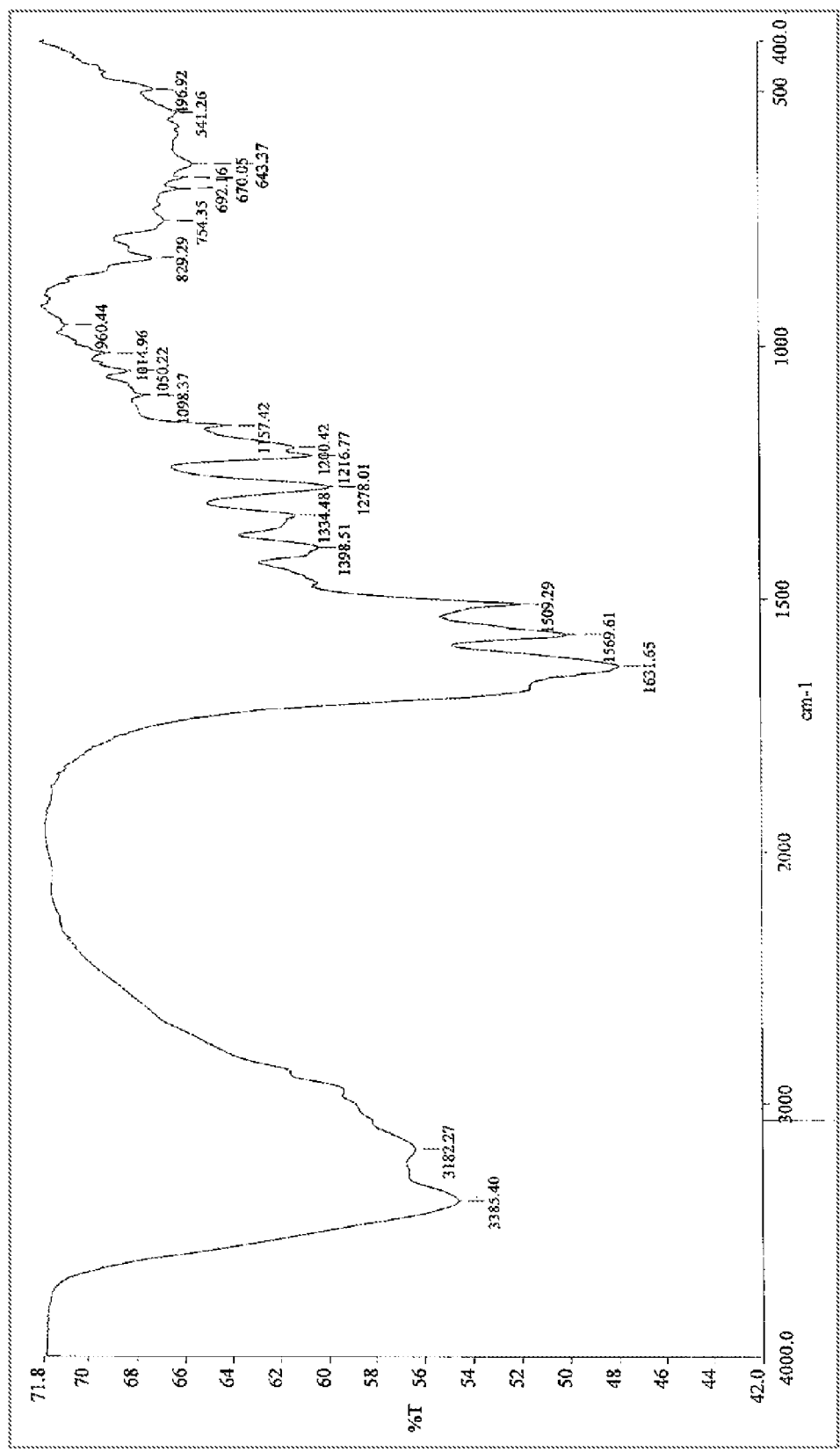

FIG. 10: illustrates IR spectrum for amorphous L-arginine salt of raltegravir.

SUMMARY OF THE INVENTION

The present invention provides novel crystalline salts of raltegravir, viz., meglumine salt, erbumine salt, ammonium salt and tris salt; an amorphous L-arginine salt of raltegravir and process for their preparation.

DETAIL DESCRIPTION OF THE INVENTION

The present invention provides novel crystalline salts of raltegravir, viz., meglumine salt, erbumine salt, ammonium salt and tris salt; an amorphous L-arginine salt of raltegravir and process for their preparation. The invention also encompasses various polymorphic forms, hydrates and solvates of all the salts of raltegravir covered by the invention.

In one embodiment, the invention provides a novel crystalline meglumine salt of raltegravir, represented by formula I, which is characterized by XRPD (X-ray powder diffractogram) which comprises of peaks expressed as 2θ at 7.9, 8.2, 8.9, 12.4, 13.4, 14.9, 15.9, 17.2, 19.4, 21.5, 21.9, 22.4, 22.8, 25.0, 26.3 and 27.1±0.2 degrees. The XRPD of crystalline meglumine salt of raltegravir is depicted in FIG. 1

Formula I

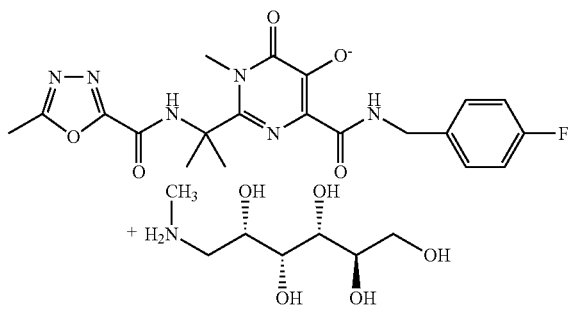

The IR spectrum of crystalline meglumine salt is as depicted in FIG. 2 which exhibits major peaks at 3584.4, 3492.7, 3336.2, 3249.7, 2951.3, 2919.3, 1703.5, 1686.9, 1638.4, 1557.8, 1524.0, 1509.1, 1441.3, 1420.3, 1343.4, 1242.3, 1218.7, 1201.9, 1097.8, 1075.0, 1050.2, 1017.2, 945.1, 908.9, 846.2, 692.7 and 648.9 cm$^{-1}$.

In another embodiment, the present invention provides a process for preparation of meglumine salt of raltegravir, which comprises of treating raltegravir with meglumine in an alcohol solvent followed by addition of an anti-solvent to precipitate the meglumine salt.

The alcohol solvent is selected from the group of lower alcohols such as methanol, ethanol, n-propanol, isopropanol and the like, most preferably methanol.

The anti solvent is selected from ethers such diethyl ether, diisopropyl ether, ethyl methyl ether, diethyl ether; cyclic ethers such as tetrahydrofuran, dioxane; most preferably diisopropyl ether.

The molar ratio of meglumine with respect to raltegravir is in the range of 0.5 to 10, preferably 1 to 3, most preferably 1.2.

The salt formation is carried out at a temperature of 10 to 100° C., most preferably at 20° C. The crystalline solid salt which precipitates out is isolated by techniques known in prior art such as filtration, centrifugation etc.

In another embodiment, the invention provides a novel crystalline erbumine salt of raltegravir, represented by formula II, which is characterized by XRPD (X-ray powder diffractogram) which comprises of peaks expressed as 2θ at 4.2, 8.4, 9.1, 11.7, 12.6, 13.8, 15.2, 16.9, 18.0, 18.4, 18.8, 19.0, 20.8, 21.2, 22.0, 22.4 and 22.7±0.2 degrees. The XRPD of crystalline erbumine salt of raltegravir is depicted in FIG. 3.

Formula II

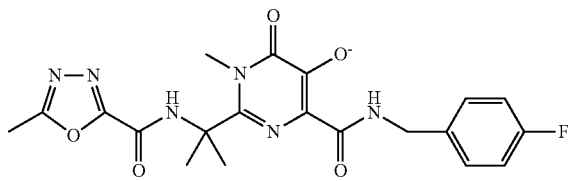

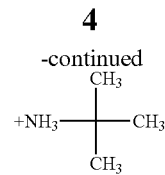

The IR spectrum of crystalline erbumine salt is as depicted in FIG. 4 which exhibits major peaks at 3436.5, 3240.7, 2944.0, 2972.0, 2878.7, 1659.1, 1623.0, 1574.7, 1550.1, 1510.9, 1490.6, 1397.0, 1371.7, 1341.7, 1297.4, 1267.6, 1218.6, 1158.8, 1050.7, 1006.2, 952.4, 869.8, 828.0, 771.9, 741.7 and 633.8 cm$^{-1}$.

In another embodiment, the present invention provides a process for preparation of erbumine salt of raltegravir, which comprises of treating raltegravir with tert-butyl amine in an alcohol.

The alcohol is selected from the group of lower alcohols such as methanol, ethanol, n-propanol, isopropanol and the like, most preferably methanol.

The molar ratio of tertiary butyl amine with respect to raltegravir is in the range of 1 to 10, preferably 1 to 3, most preferably 1.2.

The salt formation is carried out at a temperature of 10-100° C., preferably at 18-20° C. The crystalline solid obtained is isolated by conventional techniques known in the art such as filtration, centrifugation etc.

In another embodiment, the invention provides a novel crystalline ammonium salt of raltegravir, represented by formula III, which is characterized by XRPD (X-ray powder diffractogram) which comprises of peaks expressed as 2θ at 6.0, 8.8, 9.9, 11.3, 12.4, 16.2, 17.2, 17.7, 18.7, 19.4, 20.0, 20.8, 21.6, 24.6, 25.4, 26.4±0.2 degrees. The XRPD of crystalline ammonium salt of raltegravir is depicted in FIG. 5.

Formula III

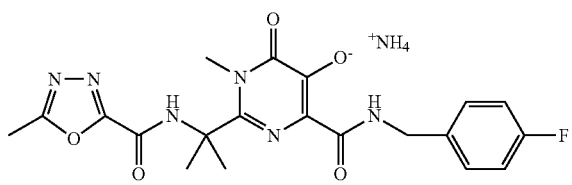

The IR spectrum of crystalline ammonium salt is as depicted in FIG. 6 which exhibits major peaks at 3383.6, 3213.5, 3001.1, 2938.9, 1683.6, 1645.8, 1603.8, 1571.1, 1535.0, 1509.7, 1468.0, 1420.2, 1394.4, 1352.4, 1271.4, 1250.3, 1218.2, 1195.4, 1097.7, 1048.0, 1017.1, 958.6, 857.2, 828.9, 727.1, 693.5 and 645.7 cm$^{-1}$.

In another embodiment, the present invention provides a process for preparation of ammonium salt of raltegravir, which comprises of treating raltegravir with ammonia in an alcohol solvent.

The alcohol is selected from the group of lower alcohols such as methanol, ethanol, n-propanol, isopropanol and the like, most preferably methanol.

Ammonia is employed in gaseous form or in the form of alcoholic solution. Preferably gaseous ammonia is used.

The salt formation is carried out at a temperature of 10-100° C., preferably at 20-30° C. The solid obtained is isolated by conventional techniques known in the art such as filtration, centrifugation etc.

In another embodiment, the invention provides a novel crystalline tris salt of raltegravir, represented by formula IV, which is characterized by XRPD (X-ray powder diffractogram) which comprises of peaks expressed as 2θ at 7.6, 7.9, 8.1, 11.3, 11.6, 13.4, 14.9, 15.4, 15.8, 15.9, 16.2, 20.0, 22.4, 22.8, 23.3, 23.8, 25.0, 25.3, 26.5, 27.0, 29.2, 29.9, 32.3±0.2 degrees. The XRPD of crystalline tris salt of raltegravir is depicted in FIG. 7.

Formula IV

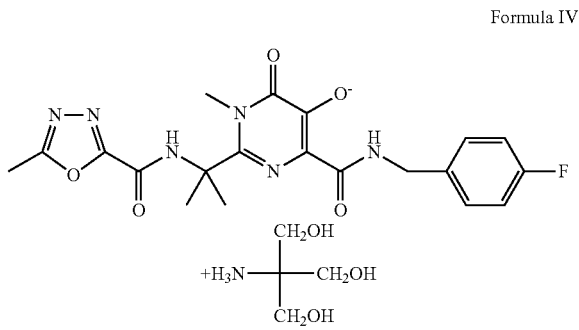

The IR spectrum of crystalline tris salt is as depicted in FIG. 8 which exhibits major peaks at 3584.8, 3494.1, 3340.7, 3303.4, 2949.6, 3000.8, 1703.3, 1686.6, 1637.7, 1599.8, 1556.7, 1536.2, 1523.5, 1508.7, 1462.4, 1421.5, 1387.6, 1344.2, 1251.4, 1218.5, 1201.0, 1159.5, 1098.6, 1020.3, 1003.7, 949.5, 875.1, 855.1, 829.1, 810.9, 795.9, 768.2, 719.5, 692.9 and 641.4 $cm^{-1}$.

In another embodiment, the present invention provides a process for preparation of tris salt of raltegravir, which comprises of treating raltegravir with tris(hydroxymethyl)aminomethane also commonly known as tris in an alcohol solvent.

The alcohol is selected from the group of lower alcohols such as methanol, ethanol, n-propanol, isopropanol and the like, most preferably methanol.

The molar ratio of tris buffer with respect to raltegravir is in the range of 1 to 10, preferably 1 to 3, most preferably 1.2.

The salt formation is carried out at a temperature of 10-100° C., preferably at 18-20° C. The crystalline solid obtained is isolated by conventional techniques known in the art such as filtration, centrifugation etc.

In another embodiment, the invention provides a novel amorphous L-arginine salt of raltegravir, represented by formula V, which is characterized by XRPD (X-ray powder diffractogram) which comprises of a single broad peak expressed as 2θ at about 20.2±0.2 degrees. The XRPD of amorphous L-arginine salt of raltegravir is depicted in FIG. 9.

Formula V

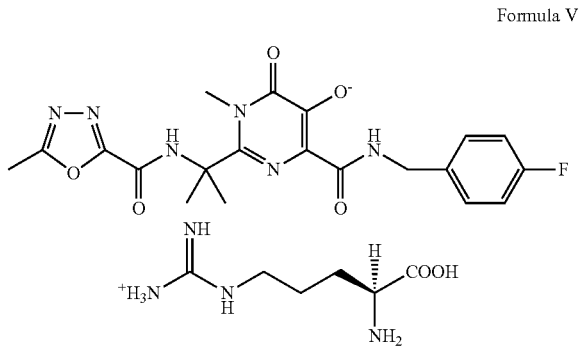

The IR spectrum of amorphous L-arginine salt of raltegravir is as depicted in FIG. 10 which exhibits major peaks at 3385.4, 3182.2, 1631.6, 1569.6, 1509.2, 1398.5, 1334.4, 1278.0, 1216.7, 1200.4, 1157.4, 1098.3, 1050.2, 1014.9, 960.4, 829.2, 754.3, 692.1, 670.0, 643.3, 541.2 and 496.9 $cm^{-1}$.

In another aspect, the present invention provides a process for preparation of amorphous L-arginine salt of raltegravir, which comprises of treating raltegravir with L-arginine in an alcohol solvent followed by addition of anti-solvent.

The alcohol is selected from the group of lower alcohols such as methanol, ethanol, n-propanol, isopropanol and the like, most preferably methanol. The anti-solvent employed for precipitation of L-arginine salt is selected from ethers such diethyl ether, diisopropyl ether, ethyl methyl ether, diethyl ether; cyclic ethers such as tetrahydrofuran, dioxane; most preferably diisopropyl ether.

The molar ratio of L-arginine with respect to raltegravir is in the range of 1 to 10, preferably 1.2.

The salt formation is carried out at a temperature of 10-100° C., preferably at 18-20° C. The amorphous solid obtained is isolated by conventional techniques known in the art such as distillation, filtration, centrifugation, spray drying, lyophilization etc.

The invention is further defined by reference to the following examples. It is apparent to those skilled in the art that many modifications, both to materials and methods, may be practiced without departing from scope of the invention.

EXAMPLES

The X-ray diffraction patterns were measured using Philips X'Pertpro machine with following measurement parameters:
Scan axis: Gonio
Step size: 0.0080°
Scan type: continuous
Divergence slit size: 0.2393°
Anode material: Cu
Radiation type: K-alpha 1
Scan: 3.49 to 40° 2θ
Spinning: Yes
Measurement temperature: 25° C.

Example 1

Preparation of Meglumine Salt of Raltegravir 2.0 g of raltegravir was dissolved in 20 ml of methanol. 1.05 g of meglumine was added to the slurry and the mixture was stirred at 20° C. for 10-15 hours. 40 ml of diisopropyl ether was added to the solution to precipitate the salt. The resulting mixture was stirred for 3-4 hours at 20-25° C. and filtered. The solid obtained was washed with 1:1 mixture of diisopropyl ether and methanol and dried under vacuum.
Yield=1.5 g
Purity=99.5%

Example 2

Preparation of Erbumine Salt of Raltegravir 2.0 g of raltegravir was stirred in 20 ml of methanol. 0.4 g of tertiary butyl amine was added and the reaction mixture was stirred at 18° C. for 0.5 hours. The reaction mass was filtered and solid obtained was washed with methanol and dried under reduced pressure.
Yield=1.1 g
Purity=91.3%

Example 3

Preparation of Ammonium Salt of Raltegravir 25 ml of methanol was added to 3.0 g of raltegravir and stirred to obtain slurry Ammonia gas was purged through the slurry at 20-30° C. for 15 minutes to obtain a clear solution. The solution was cooled to 10-15° C., stirred for 1.5 hours. The solid obtained was filtered, washed with cold methanol and dried under reduced pressure.
Yield=2.0 g
Purity=98.8%

Example 4

Preparation of Tris Salt of Raltegravir 20 ml of methanol was added to 2.0 g of raltegravir and stirred to obtain slurry. 0.65 g of tris buffer was added and the reaction mixture was stirred at 18° C. for 12 hours to precipitate the salt. The reaction mixture was filtered and solid obtained was washed with methanol and dried under reduced pressure.
Yield=1.18 g
Purity=98.8%

Example 5

Preparation of L-Arginine Salt of Raltegravir 20 ml of methanol was added to 2.0 g of raltegravir and stirred to obtain slurry. 0.94 g of L-arginine was and added and the mixture was stirred at 20° C. for 25 hours. The solution was filtered and 50 ml of diisopropyl ether was added. The mixture was concentrated under reduced pressure to obtain a sticky residue. 50 ml of acetonitrile was charged to the residue and the mixture was stirred at 20° C. for 1 hour. The solid obtained was filtered, washed with acetonitrile and dried under reduced pressure to afford amorphous product.
Yield=2.0 g
Purity=93%

The invention claimed is:

1. A crystalline meglumine salt of raltegravir, represented by formula I,

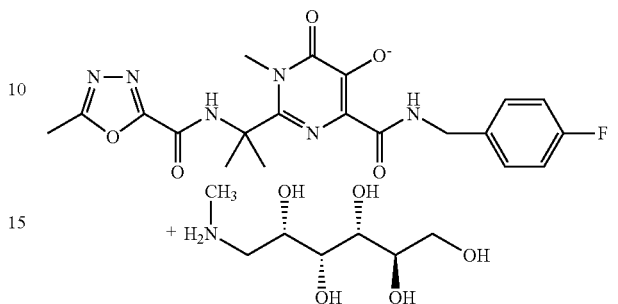

Formula I which is characterized by XRPD (X-ray powder diffractogram) comprising of peaks expressed as 2θ at 7.9, 8.2, 8.9, 12.4, 13.4, 14.9, 15.9, 13.2, 19.4, 21.5, 21.9, 22.4, 22.8, 25.0, 26.3 and 27.1±0.2 degrees.

2. A process for preparation of crystalline meglumine salt of raltegravir of claim 1, which comprises of treating raltegravir with meglumine in an alcohol solvent followed by addition of an anti-solvent to precipitate the meglumine salt.

3. A process according to claim 2, wherein the alcohol solvent is selected from methanol, ethanol, n-propanol and isopropanol.

4. A process according claim 3, wherein the alcohol solvent is methanol.

5. A process according to claim 2, wherein the anti-solvent is selected from ethers such diethyl ether, diisopropyl ether, ethyl methyl ether, diethyl ether; cyclic ethers such as tetrahydrofuran and dioxane.

6. A process according to claim 5, wherein the anti-solvent is diisopropyl ether.

7. A process according to claim 2, wherein the molar ratio of meglumine with respect to raltegravir is in the range of 1 to 3.

* * * * *

UNITED STATES PATENT AND TRADEMARK OFFICE
CERTIFICATE OF CORRECTION

Page 1 of 1

PATENT NO.        : 9,163,009 B2
APPLICATION NO.   : 14/009178
DATED             : October 20, 2015
INVENTOR(S)       : Purna Chandra Ray et al.

It is certified that error appears in the above-identified patent and that said Letters Patent is hereby corrected as shown below:

In the claims

Column 8, Line 22, Claim 1, delete "13.2," and insert -- 17.2, --

Signed and Sealed this
Fifteenth Day of March, 2016

Michelle K. Lee
*Director of the United States Patent and Trademark Office*